United States Patent [19]

Kajino

[11] Patent Number: 5,355,734
[45] Date of Patent: Oct. 18, 1994

[54] LIFE PREDICTING GAUGE FOR STRUCTURE AND LIFE PREDICTING METHOD EMPLOYING THE SAME

[75] Inventor: Katsuhiro Kajino, Kanagawa, Japan

[73] Assignee: Kabushiki Kaisha Komatsu Seisakusho, Japan

[21] Appl. No.: 955,862

[22] PCT Filed: Jun. 12, 1991

[86] PCT No.: PCT/JP91/00793

§ 371 Date: Dec. 9, 1992

§ 102(e) Date: Dec. 9, 1992

[87] PCT Pub. No.: WO91/19968

PCT Pub. Date: Dec. 26, 1991

[30] Foreign Application Priority Data

Jun. 12, 1990 [JP] Japan ................ 2-151667

[51] Int. Cl.$^5$ .................................. G01B 7/16
[52] U.S. Cl. .................................. 73/775; 73/787
[58] Field of Search ................ 73/799, 786, 787, 775

[56] References Cited

U.S. PATENT DOCUMENTS

| | | | |
|---|---|---|---|
| 2,920,480 | 1/1960 | Haas | 73/787 |
| 3,136,154 | 6/1964 | Christensen | 73/787 |
| 3,272,003 | 9/1966 | Harting | 73/787 |
| 3,602,041 | 8/1971 | Weinert | 73/787 |
| 3,786,679 | 1/1974 | Crites | 73/775 |
| 3,979,949 | 9/1976 | Smith | 73/799 |

FOREIGN PATENT DOCUMENTS

| | | | |
|---|---|---|---|
| 52-32588 | 3/1977 | Japan | |
| 53-33681 | 3/1978 | Japan | |
| 56-117142 | 9/1981 | Japan | |
| 56-117165 | 9/1981 | Japan | 73/799 |
| 61-56538 | 4/1986 | Japan | |
| 63-122928 | 5/1988 | Japan | 73/799 |

Primary Examiner—Robert Raevis
Attorney, Agent, or Firm—Ronald P. Kananen

[57] ABSTRACT

The present invention is intended to facilitate prediction of the life of a structure, such as a frame of a dump truck and so forth without requiring cumbersome calculations. A gauge (2, 3 or 4) for predicting a life of a structure comprises a gauge main body of a thin plate form having annular ring portions (5, 6) of substantially the same configuration at both ends and a strip-like connecting portion (7) integrally connecting the annular ring portions and formed with V-shaped cut-outs (8, 8) at the intermediate portion in opposition to each other. The gauge main body has a shorter life than the life of the structure (1) to be predicted. A crack gauge is fitted between the mutually opposing cut-outs. The gauge is fixed on a predetermined position on the structure by way of welding or so forth. A breaking time of the gauge can be obtained from a variation of a measured resistance of the crack gauge. Based on the breaking period, the life of the structure (1) is predicted.

20 Claims, 3 Drawing Sheets

LIFE PREDICTING GAUGE FOR STRUCTURE AND LIFE PREDICTING METHOD EMPLOYING THE SAME

FIELD OF THE INVENTION

The present invention relates to a gauge for predicting a useful life of a structure subjected to a varying load, such as a frame of a constructional large size dump truck and so forth.

BACKGROUND OF THE INVENTION

A constructional large size dump track is formed by mounting a frame on front and further rear wheels and defines a driver's compartment and a vessel for transporting earth, sand or so forth. The frame is subject bending load and a torsional load to possibly cause breakage due to fatigue.

On the other hand, the bending and torsional loads acting on the frame can be significantly differentiated depending upon load weight on the vessel, road surface condition, vehicle speed and so forth. Therefore, it is practically not possible to predict the timing for breakage by fatigue, i.e. a useful life of the frame.

Therefore, in the prior art, a strain gauge is fitted on the frame for measuring a distortion of the strain gauge as an actual strain by means of a measuring equipment during operation for a long period. Based on the measured value, fatigue damage of the frame is calculated through a cumbersome calculation, such as by frequency processing and so forth to predict the useful life.

In such method of for predicting the useful life, of a member it becomes necessary to perform a cumbersome calculation, such as frequency processing and so forth, on the basis of the measured values. Also, only data, representative of an operational condition while the measurement is performed by means of the measuring equipment, can be obtained.

SUMMARY OF THE INVENTION

In view of the problems set forth above, it is an object of the present invention to provide a novel gauge for predicting a life of a structure which facilitates prediction of the life of the structure without requiring a cumbersome calculation as required in the prior art, and to provide a method for predicting the life employing the same.

In order to accomplish the above-mentioned objects, there is provided, in accordance with the first aspect of the invention, a gauge for predicting a life of a structure comprising a gauge main body of thin plate form having annular ring portions of substantially the same configuration at both ends and a strip-like connecting portion integrally connecting the annular ring portions and formed with V-shaped cut-outs at an intermediate portion in opposition to each other, the gauge main body having a shorter life than the life of the structure to be predicted and a crack gauge fitted between the mutually opposing cut-outs.

Also, in order to accomplish the above-mentioned object, there is provided, in accordance with the present invention, a method for predicting a life of a structure comprising the steps of rigidly fixing a gauge as defined to a predetermined portion of the structure, obtaining a breaking period of the gauge on the basis of a variation of a resistance, and predicting a life of the structure on the basis of the breaking period thus obtained.

As set forth above, according to the present invention, since the life of the structure can be predicted by mounting the gauge having a shorter fatigue life than the structure on the structure, by detecting the cracking condition of this gauge based on a variation of the resistance of the crack gauge and thus deriving a breaking period, the life of the structure can be easily predicted without requiring cumbersome calculations as required in the prior art.

The above-mentioned and other objects, aspects and advantages of the present invention will become clear to those skilled in the art from the discussion described and illustrated in connection with the accompanying drawings which illustrate preferred embodiments meeting with the principles of the invention.

Fig,.4 is an enlarged view of the crack gauge; and

Figure 5:
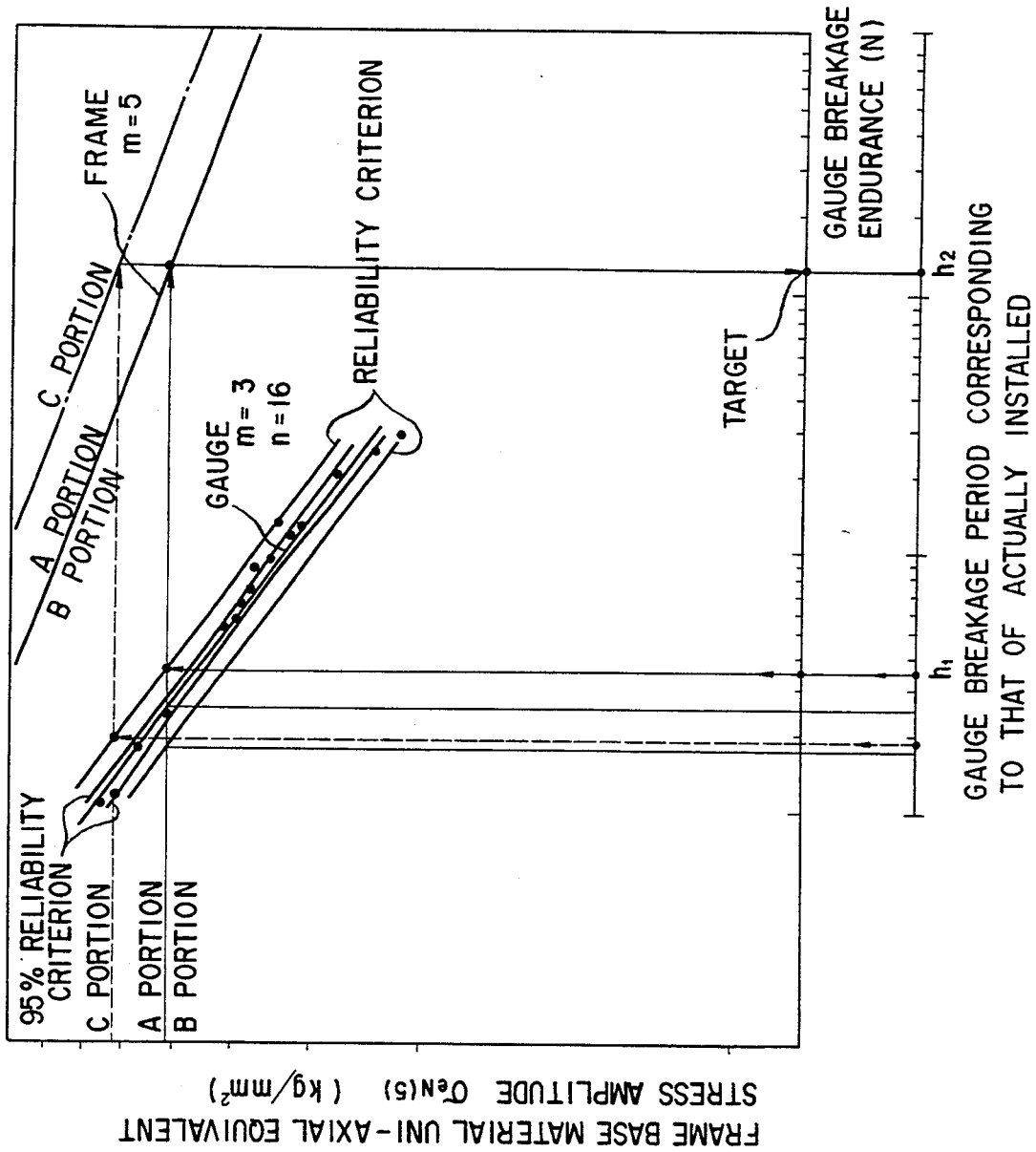

FIG. 5 is a chart showing predicted life of various portions of the structure.

DESCRIPTION OF THE PREFERRED EMBODIMENT

The present invention will be discussed hereinafter in detail with reference to the accompanying drawing.

Figure 1:
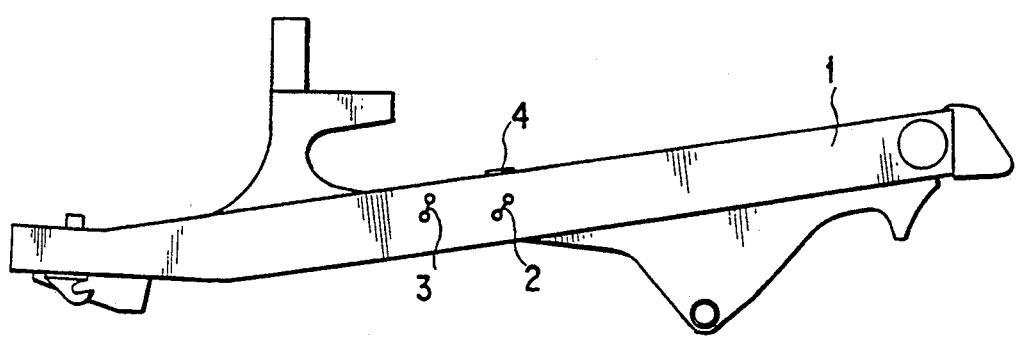
Fig. 1 is a schematic side elevation showing a gauge for predicting a life according to the present invention mounted on a structure, a life of which is to be predicted.
Figure 2:
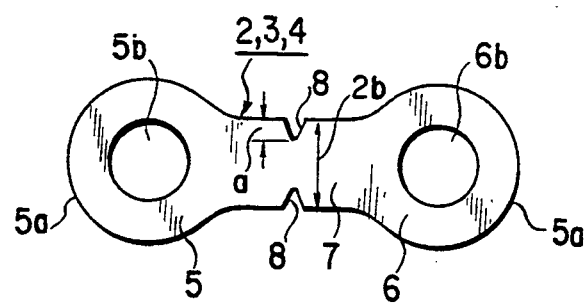
FIG. 2 is a plan view of a main body of the gauge.

As shown in FIG. 1, first and second torsional load detecting gauges 2 and 3 are mounted on a frame 1 at a portion where a torsional force is active, such as a side, by way of welding. Also, a bending load detecting gauge 4 is mounted on the frame 1 at a portion where a bending force is active, such as an upper surface, by way of welding.

A main body of each of the gauges 2, 3 and 4 comprises a annular ring portion 5 at one side, a annular ring portion 6 at the other side and a connecting piece 7 integrally connecting the annular ring portions 5 and 6. The substantially circular ring shaped configuration of the annular ring portions 5 and 6 avoid formation of the critical point and thus successfully prevents the stress to be exerted on the main body of each of the gauges 2, 3 and 4 from concentrating at any portion thereof. The connecting piece 7 is formed with V-shaped cut-outs 8, 8 at essentially the intermediate portion thereof, which cut-outs 8, 8 are arranged in opposition to each other so that a fatigue breakage can be easily caused at the position of the cut-outs 8, 8. The main body of the gauge is rigidly mounted on the frame 1 by welding the outer peripheral portions 5a and 6a of the annular ring portions 5 and 6 at one and the other sides and the inner peripheral portions 5b and 6b of the annular ring portions 5 and 6.

The depth of the cut-outs 8 of the gauges 2, 3 and 4 and the width $2b$ of the connecting piece 7 are determined by the following manner.

Here, it should be noted that the following discussion is given for the case where the overall length of the gauge is 80~100 mm, thickness is 2.3~3.2 mm, and the material is SS41P.

In case that a stress amplitude is $\sigma$ kg/mm$^2$ a stress endurance N of the stress amplitude up to occurrence of breakage of the connecting piece 7, in which the cut-outs 8 are formed, can be expressed by the following equation:

$$N = 5.16 \times 10^9 \times (2.15 \times 10^6) \xi \times \sigma^4 \quad (1)$$

wherein $\xi = a/b$

N is typically required to be greater than or equal to $10^5$ times. Therefore, in order to monitor the load within a short period, $\xi$ is required to be large.

On the other hand, since a range $\Delta K th$ of a crack propagation critical stress expansion coefficient is $$\Delta K th = \sigma \sqrt{\pi a} \geq 10 \text{ (kg/mm}^{3/2})$$

it becomes necessary to satisfy $$a \geq 31.8/\sigma^2 \text{ (mm)} \quad (2)$$

Then, based on a stress amplitude $\sigma$ and a frequency at a reference load condition, the dimensions a and b satisfying the foregoing equations (1) and (2) are determined.

Figure 3:
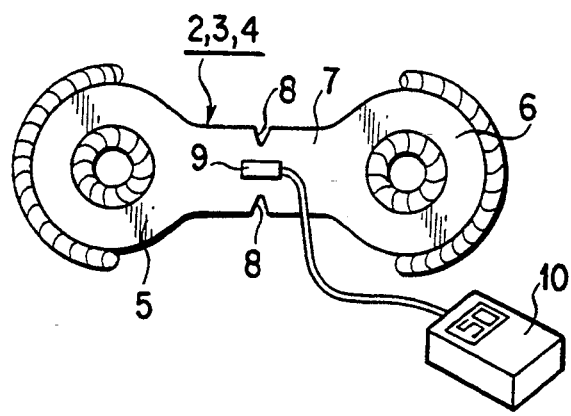
FIG. 3 is a front elevation of the gauge main body of FIG. 2 showing a condition mounting a crack gauge thereon and a portion thereof to be welded onto the structure.

As shown in FIG. 3, a crack gauge 9 is fitted on the connecting piece 7 of each gauge 2, 3 and 4 at a position between the cut-outs 8, 8 for measuring variation of a resistance of the crack gauge 9 by means of a tester 10.

Figure 4:
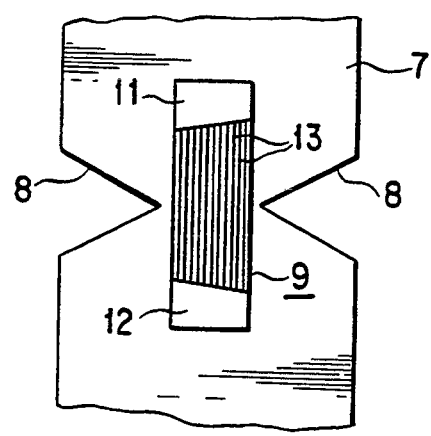

As shown in FIG. 4, the crack gauge 9 comprises a strip 11 at one side, a strip 12 at the other side and a plurality of, elementary wires 13 for example, thirteen in number, connecting therebetween. As a result of checking the overall length of the crack in the gauge, a number of broken elementary wires 13 and the resistances thereof, the following table can be attained.

TABLE

| Number of Broken Elementary Wire | Overall Length of Crack | Resistance |
| --- | --- | --- |
| 0 | $\leq 1$ mm | 9$\Omega$ |
| 3 | 1.9 mm | 11$\Omega$ |
| 5 | 2.5 mm | 13~19$\Omega$ |
| 7 | 3.2 mm | 33~38$\Omega$ |

From this, it should be appreciated that the occurrence of the crack, crack propagation, crack extension over overall width in each of the gauges 2, 3 and 4 can be accurately detected.

Upon actual work at the actual working site, the measurement of the resistance by means of the tester 10 is performed for every given period. The measured value is written on a check sheet.

For instance, as shown in the following table, with respect to each crack gauge, the resistance and a service meter indication (a value of an odometer of the engine) are written in.

TABLE

| Year/Month/Day | Resistance ($\Omega$) | Service Meter (h) |
| --- | --- | --- |
| First Gauge (2) | | |
| '89/12/20 | 50 | 200 |
| '90/1/18 | 50 | 600 |
| '90/2/25 | 50 | 1050 |
| '90/3/19 | 70 | 1440 |
| '90/4/24 | 110 | 1900 |
| '90/5/16 | 190 | 2380 |
| '90/6/17 | 350 | 2880 |
| '90/07/21 | 670 | 3420 |
| Second Gauge (3) | | |
| '89/12/20 | 50 | 200 |
| '90/1/18 | 50 | 600 |
| '90/2/25 | 110 | 1050 |
| '90/3/19 | 670 | 1540 |
| '90/4/24 | Break | 2100 |
| Third Gauge (4) | | |
| '89/12/20 | 50 | 200 |
| '90/1/18 | 50 | 600 |
| '90/2/25 | 500 | 1050 |
| '90/3/19 | Break | 1200 |

The foregoing measurement is performed with respect to a plurality of vehicles, e.g. three vehicles.

From the data thus obtained, the periods to breakage of the gauges are collected to derive a predicted life of an actually installed frame according to a chart illustrated in FIG. 5.

The life of the frame is thus predicted. If the frame life is too short, an improvement of the frame life is attained by reducing the vessel load weight, smoothing the road surface, and limiting the vehicle speed so as to reduce the load acting on the frame.

In the discussion given hereabove, the gauge breaking period can be obtained through the following manner. At first, the gauges are fitted at the same positions of the vehicles of the same model working at the same working site. Then, five to ten data are obtained with respect to the gauge number and gauge breaking periods. Through Weibull analysis of the data, the gauge breaking period of the specific model and specific portions at the specific site are obtained.

For example, at a certain site, the gauges are mounted at A portions of ten vehicles of the model of H03255-5. Through Weibull analysis of the breaking period of the 10 gauges, the breaking time is obtained.

Also, the predicted life of the actually installed frame can be obtained in such a manner that when the gauge breaking period is $h_1$, it is applied in the chart of FIG. 5 as shown by the arrow to obtain the predicted life of the actual vehicle (in case of A portion). In this case, the sensitivity of the gauge becomes $h_2 h_1$ times of that of the frame.

On the other hand, in the drawing, m is a reciprocal (stress $S^m \times$ stress endurance N = constant C) of a gradient of stress endurance diagram, which is different in the gauge and the frame.

What is claimed is:

1. A gauge for predicting a life of a structure comprising:

a gauge main body formed of a thin plate having annular ring portions of substantially the same configuration located at both ends of said thin plate and having a strip-like connecting portion integrally connecting said annular ring portions, said strip-like connecting portion formed with V-shaped cut-outs at an intermediate portion in opposition to each other, said gauge main body having a fatigue characteristic related to a fatigue characteristic of said structure but having shorter life than a life of said structure; and a crack gauge fitted between said V-shaped cut-outs.

2. A gauge as set forth in claim 1, wherein, assuming a depth of said cut-out is a mm, a lateral width of said strip-like connecting portion is 2b mm, a stress amplitude in the longitudinal direction of the gauge is $\sigma$ kg/mm², an endurance of the stress amplitude at the connecting portion with the cut-out is N and a range of a crack propagation critical stress expansion coefficient is $\Delta Kth$, the respective elements establish the following relationship:

$$N = 5.16 \times 10^9 \times (2.15 \times 10^6)^\xi \times \sigma^{-4} \qquad (1)$$

wherein $\xi = a/b$; and $$a \geq 31.8/\sigma^2 \, (\text{mm}) \qquad (2)$$

wherein $$\Delta Kth = \sigma \sqrt{\pi a} \geq 10 \, (\text{kg/mm}^{3/2}).$$

3. A method for predicting a life of a structure comprising the steps of:
 preparing a gauge having a fatigue characteristic related to a fatigue characteristic of said structure, said gauge breaking at a first time in response to a repeatedly applied stress load and said structure breaking at a second time in response to said repeatedly applied stress load, said first time earlier than said second time;
 rigidly fixing said gauge to a predetermined portion on said structure;
 determining said first time at which period said gauge breaks on the basis of a variation of a resistance in said gauge; and
 predicting said second time at which point said structure will break on the basis of the first time thus determined.

4. A method for predicting a life of a structure as set forth in claim 3, wherein said step of fixing comprises the step of fixing a plurality of gauges to a respective plurality of predetermined positions on said structure.

5. A method for predicting a life of a structure as set forth in claim 3, wherein said step of fixing comprises the step of fixing said gauge to the predetermined position on said structure by welding outer arc portions and inner arc portions of annular ring portions of said gauge to said structure.

6. A gauge for predicting a life of a structure comprising:
 a gauge main body to be fitted on a portion of said structure whose life is to be predicted, said gauge main body having a fatigue characteristic modeled to a fatigue characteristic of said structure in response to a common repeated stress load to said structure, said gauge main body breaking within a period of life of said structure;
 means cooperated with said gauge to cause a specific portion of said gauge main body to crack in response to said common repeated stress load exerted on said gauge main body;
 means associated with said specific portion of said gauge main body for varying an electrical characteristic depending upon a condition of said crack and for generating an electrical signal indicating a magnitude of damage of said gauge main body, wherein a variation of said electrical signal reflects a stress condition on said structure; and
 means for predicting said period of life of said structure prior to the expiration of said period of life based upon said gauge main body having a characteristic modeled to said structure.

7. A gauge as set forth in claim 6, wherein said gauge main body is comprised of a material having a uni-axial equivalent stress amplitude variation characteristic for causing said gauge main body to break due to a repeated stress exerted thereto at an earlier time than when said structure breaks wherein the life of said structure is predicted based upon the life of said gauge main body and said fatigue characteristic of said structure.

8. A gauge as set forth in claim 6, wherein said means to cause a specific portion of said gauge main body to crack provides a stress characteristic for said gauge main body to cause a concentration of stress at said specific portion.

9. A gauge as set forth in claim 8, wherein said means for defining a specific portion of said gauge main body defines said specific portion at an intermediate position between the longitudinal ends thereof, at which said gauge main body is rigidly secured on said portion of said structure.

10. A gauge as set forth in claim 6, wherein said means for causing a variation of electrical characteristics is a crack gauge varying resistance depending upon the magnitude of the crack formed at said specific portion.

11. A method for predicting a life of a structure repeatedly subjected to stress, said structure having known fatigue characteristics at respective portions thereof including a life predicting portion at which the life is to be predicted, comprising the steps of:
 providing a gauge having known fatigue characteristics with shorter life than the possible life period of said structure, said gauge defining a stress concentrating portion, to which the stress exerted is concentrated;
 rigidly fitting said gauge on said life predicting portion of said structure so that said gauge experiences the common stresses with the life predicting portion of said structure;
 monitoring damaging condition of said gauge at every given timing to detect breakage of said gauge;
 measuring an elapsed time until detection of the breakage of said gauge for deriving a breakage period of said gauge for establishing a fatigue model of said structure; and
 predicting a remaining life of said structure on the basis of said fatigue model established in connection with said breakage period of said gauge and said known fatigue characteristics of said structure.

12. A method as set forth in claim 11, wherein said known fatigue characteristics of said gauge is defined by a cut-out formed at said stress concentrating portion thereof.

13. A method as set forth in claim 12, wherein the depth of said cut-out is determined in such a manner that assuming a depth of said cut-out is a mm, a lateral width of said strip-like connecting portion is 2b mm, a stress amplitude in the longitudinal direction of the gauge is $\sigma$ kg/mm², an endurance of the stress amplitude at the connecting portion with the cut-out is N and a range of a crack propagation critical stress expansion coefficient is $\Delta Kth$, the respective elements establish the following relationship:

$$N = 5.16 \times 10^9 \times (2.15 \times 10^6)^\xi \times \sigma^{-4} \qquad (1),$$

wherein $\sigma = a/b$; and $$a \geq 31.8/\sigma^2 \text{(mm)} \quad (1),$$

wherein $$\Delta K_{th} = \sigma \sqrt{\pi a} \geq 10 \text{ (kg/mm}^{3/2}\text{)}.$$

14. A method as set forth in claim 11, which further comprises the step of providing means for varying an electric characteristic depending upon the damage condition of said gauge, and said monitoring of the damage condition of said gauge is performed by monitoring variation of said electric characteristic.

15. A method as set forth in claim 14, wherein said electric characteristic is a resistance.

16. A method for predicting a life of a structure repeatedly subjected to stress, said structure having known fatigue characteristics at respective portions thereof including a life predicting portion at which the life is to be predicted, comprising the steps of:

providing a gauge having known fatigue characteristics with higher sensitivity of stress than said structure, said gauge defining a stress concentrating portion, to which the stress exerted is concentrated;

rigidly fitting said gauge on said life predicting portion of said structure so that said gauge experiences the common stresses with the life predicting portion of said structure;

monitoring a damaging condition of said gauge at every given timing to detect breakage of said gauge;

measuring an elapsed time until detection of breakage of said gauge for deriving a breakage period of said gauge for establishing a fatigue model of said structure; and predicting a remaining life of said structure on the basis of said fatigue model established in connection with said breakage period of said gauge and said known fatigue characteristics of said structure.

17. A method as set forth in claim 16, wherein said known fatigue characteristics of said gauge is defined by a cut-out formed at said stress concentrating portion thereof.

18. A method as set forth in claim 17, wherein the depth of said cut-out is determined in such a manner that assuming a depth of said cut-out is a mm, a lateral width of said strip-like connecting portion is 2b mm, a stress amplitude in the longitudinal direction of the gauge is $\sigma$ kg/mm$^2$, an endurance of the stress amplitude at the connecting portion with the cut-out is N and a range of a crack propagation critical stress expansion coefficient is $\Delta K_{th}$, the respective elements establish the following relationship:

$$N = 5.16 \times 10^9 \times (2.15 \times 10^6)^\xi \times \sigma^{-4} \quad (1),$$

wherein $\xi = a/b$;

$$a \geq 31.8/\sigma^2 \text{(mm)} \quad (2),$$

wherein $$\Delta K_{th} = \sigma \sqrt{\pi a} \geq 10 \text{ (kg/mm}^{3/2}\text{)}.$$

19. A method as set forth in claim 16, further comprising the step of varying an electrical characteristic depending upon the damage condition of said gauge, and said step of monitoring the damage condition of said gauge is performed by monitoring variations of said electrical characteristic.

20. A method as set forth in claim 19, wherein said electrical characteristic is resistance.

* * * * *